United States Patent [19]

Hölter et al.

[11] Patent Number: 4,930,407
[45] Date of Patent: Jun. 5, 1990

[54] SENSING SYSTEM FOR CONTROLLING AIR CIRCULATION VALVES IN MOTOR VEHICLES

[75] Inventors: Heinz Hölter, Gladbeck; Hanns Rump, Unna-Massen, both of Fed. Rep. of Germany

[73] Assignee: Heniz Holter, Gladbeck, Fed. Rep. of Germany

[21] Appl. No.: 216,622

[22] PCT Filed: Oct. 10, 1987

[86] PCT No.: PCT/EP87/00592

§ 371 Date: Jun. 3, 1988

§ 102(e) Date: Jun. 3, 1988

[87] PCT Pub. No.: WO88/02704

PCT Pub. Date: Apr. 21, 1988

[30] Foreign Application Priority Data

Oct. 11, 1986 [DE] Fed. Rep. of Germany ....... 3634786
Dec. 31, 1986 [DE] Fed. Rep. of Germany ....... 8634907

[51] Int. Cl.$^5$ .............................................. B60H 1/24
[52] U.S. Cl. .............................................. 98/2.01
[58] Field of Search .................... 98/2.01, 2.11; 73/23, 73/27 R

[56] References Cited

U.S. PATENT DOCUMENTS

| | | | |
|---|---|---|---|
| 3,418,914 | 12/1968 | Finkin | 98/2.01 |
| 4,306,444 | 12/1981 | Hattori et al. | 73/23 |
| 4,352,321 | 10/1982 | Fukui et al. | 98/2.11 |
| 4,437,391 | 3/1984 | Eguchi et al. | 98/2.01 |
| 4,458,583 | 7/1984 | Fukui et al. | 98/2.01 |
| 4,478,049 | 10/1984 | Fukui et al. | 62/179 |
| 4,733,605 | 3/1988 | Hölter et al. | 98/2.11 |
| 4,742,763 | 5/1988 | Hölter et al. | 98/2.01 |

FOREIGN PATENT DOCUMENTS

| | | | |
|---|---|---|---|
| 0092195 | 10/1983 | European Pat. Off. | |
| 120753 | 10/1984 | European Pat. Off. | 98/2.01 |
| 0179625 | 4/1986 | European Pat. Off. | |
| 2903643 | 8/1980 | Fed. Rep. of Germany | 98/2.01 |
| 3304324 | 8/1984 | Fed. Rep. of Germany | 98/2.01 |
| 186513 | 11/1982 | Japan | 98/2.01 |
| 64018 | 4/1985 | Japan | 98/2.01 |
| 143214 | 6/1986 | Japan | 98/2.01 |

Primary Examiner—Hezron E. Williams
Assistant Examiner—Joseph W. Roskos
Attorney, Agent, or Firm—Herbert Dubno

[57] ABSTRACT

The invention relates to a sensor with integrated signal preconditioning and switching amplifier, whose switching point variably adjusts to slow variations in the output level of the sensor, in order to compensate for the slow influences of temperature and humidity on the sensor and to adjust the switching behavior to external conditions. For this, the invention uses a system for locking the control values to the switching threshold, obtained from the integrated sensor signal.

19 Claims, 6 Drawing Sheets

CALCULATION OF $U_x$ AS AN INTEGRAL OF THE SENSOR SIGNAL $$U_x = \int_{U_{min}}^{U_{max}} \left[ VF_{(t)} \right]$$

FIG. 4

CALCULATION OF THE REFERENCE VOLTAGE $U_{ref}$ $$U_{ref} = \left[ \left( \frac{(U_x - U_r)}{\underset{(22)}{(R_1} + \underset{(21)}{R_2)}} \right) - \underset{(21)}{R_2} \right] + U_t$$

FIG. 5

SENSING SYSTEM FOR CONTROLLING AIR CIRCULATION VALVES IN MOTOR VEHICLES

FIELD OF THE INVENTION

The present invention relates to a sensing system for controlling air circulation valves in motor vehicles which includes a semiconductor as a sensor element for pollutants and as an electronic preconditioning of the sensor signal.

THE RELATED ART

Semiconductors which modify their inner resistance when pollutant and other gases are detected, are widely used.

Their operating principle is based on the fact that the sensor, together with an external resistor, form a voltage divider. The reading of the medium voltage measures the content of pollutants in the air.

Further, it is known that the semiconductor sensors are sensitive to temperature. Therefore, it has already been proposed to compensate this sensitivity to temperature, for instance, by wiring the external resistor with a NTC-resistor, whose characteristics correspond to the temperature characteristics of the sensor.

Further, it is known that the sensitivity of the sensor depends on the humidity of the air. As a rule, the sensors become more sensitive with increasing humidity. In order to compensate for the effects of temperature and humidity, a considerable effort is required to adapt the circuit arrangements.

In the use of such sensors for the control of air-circulation valves in motor vehicles, this transverse sensitivity preferably towards humidity can lead to different switch points, which are subjectively and objectively incorrect.

It has therefore been proposed to differentiate the detected voltage signals and to switch each only then when a persistent modification in the pollutant level occurs. This method eliminates all influences which can be traced back to temperature or humidity. This method, wherein only the difference level is transmitted, has however the disadvantage that in the case of long-term static situations with simultaneous high pollutant content, the switching process is cancelled after a certain time.

Besides, in this differentiation, it is very important whether the increase of the pollutant concentration occurs rapidly, slowly or even creepingly. Depending on the layout of the differentiation element, which—electrically speaking—is a high-pass filter, very slow increases in the pollutant concentration are not detected.

For instance, when the vehicle moves along a country road with clean environmental air, the presence of another vehicle becomes particularly disturbing because the sensitivity to smell has been enhanced.

In the reversed situation, in very heavy inner-city traffic, it is not desirable that the fresh-air valve of the vehicle remain almost permanently closed. Because the sensitivity towards pollutants is clearly dimished, it is desirable in this case to also decrease the response sensitivity.

Departing from this state of the art, it is the object of the present invention to create a sensor without the aforementioned disadvantages, which not only absolutely eliminates the influences of temperature and humidity, but also automatically adjusts its sensitivity towards pollutants.

A sensing system for controlling air circulation valves or motor vehicles is herein provided. The system comprises a pollutant detecting and electronic preconditioning sensor means in the form of a semiconductor, this means generating one or more signals related to a measured level of pollutants, and a switching amplifier receiving said signals, the amplifier having a variable operating switch point dependent upon the received signals, and a means for integrating the one or more signals. Through this arrangement is achieved short-term modifications of the sensor signal leading to the desired switching of the system while still permitting changing the switch point within predetermined limits accommodate temperature and humidity drift of the sensor. Additionally, the system may be adjusted to accommodate the subjective judgment of the human sense of smell such adjustment is important since it is known that the sense of smell reacts sharply to even small amounts of pollutants, if correspondingly conditioned by a previous stay in fresh air.

BRIEF DESCRIPTION OF THE DRAWINGS

Embodiment examples of the invention are described in more detail with the aid of the drawing, which shows:

FIG. 4 the formula for the calculation of the output voltage of the digital-analog converter as an integral of the sensor signal, FIG. 5 the formula for the calculation of the reference voltage, FIG. 6 the basic circuit diagram of a fourth embodiment, FIG. 7 a diagram with the sensor voltage as well as the therefrom resulting switch voltage, FIG. 8 a set-up of the sensor modified with respect to the embodiment of FIG. 6.

DETAILED DESCRIPTION

Figure 1:
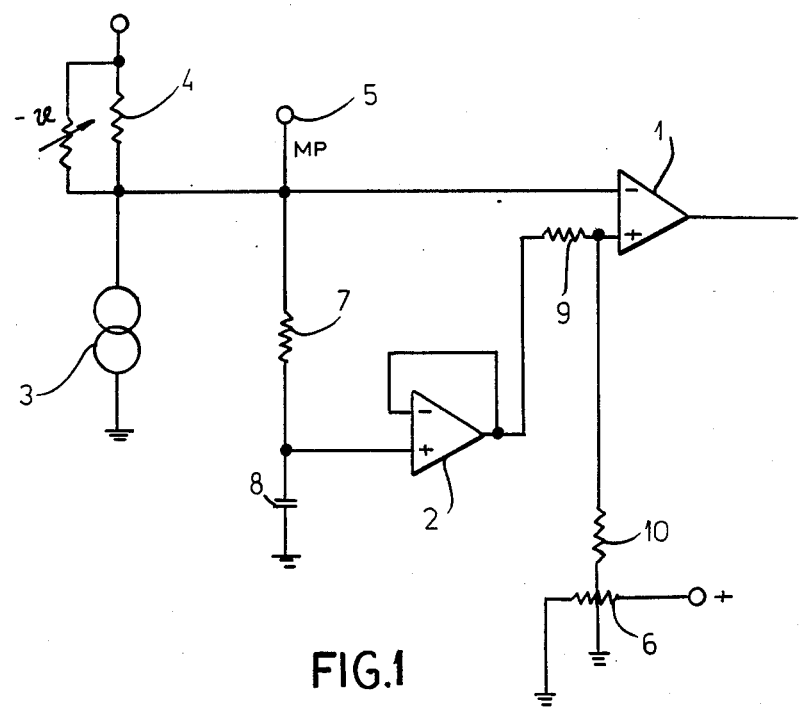
FIG. 1 the basic circuit diagram of a first embodiment.

In FIG. 1 the sensor 3 is a voltage divider with an external resistor 4, which is temperature-balanced. At the measuring point 5, the sensor voltage is read and directed to a switch amplifier 1. An operating point of the switch amplifier 1 can be set through a potentiometer 6. The potentiometer 6 can also be replaced by a resistive combination.

A sensor signal at the measuring point 5 is directed to an integrating element, consisting of resistor 7 and capacitor 8.

A time constant of this integrating element 7, 8 is selected so that short-term variations of the sensor voltage have almost no effect while long-term constant variations are very noticeable.

A time constant of approximately 2 minutes has proven to be practical.

Over an operational amplifier 2, which is connected as a noninverting impedance transformer, the integrated signal passes through a resistor 9 and reaches the switch amplifier 1, where it changes the switching threshold.

In order to avoid an inordinate increase of the influence of temperature, humidity and subjective perception leading to the fact that the sensor 3 does not trigger the switch in the case of a long-term heavy content of pollutants in the air, the influence of the above-described set-up is decreased.

According to the invention this is achieved through resistors 9 and 10 interrelating with each other and directing the switch amplifier 1 to modify its operation point.

In the preferred set-up, the resistors 9, 10 are dimensioned so that the operation point can vary within the range of ±15%.

According to the invention the following advantages are achieved:

1. The static influences of air humidity and temperature are efficiently eliminated while not adversely affecting dynamic properties of the sensor, e.g. response behavior to pollutant contents of the air.

2. When air poor in contaminants is predominant, the switch response of the sensor is more sensitive into account physiologically subjective factors.

3. In the case of permanently high pollutant contents, the switch response of the sensor is less sensitive. As a consequence the air circulation valve does not remain closed for any unacceptably long period of time, but can open again in stages when relatively low levels of air pollutant reoccur. This arrangement simplifies regulation of climate inside the passenger cabin, especially with respect to evacuation of humidity. In turn, the danger of fogged over windows is clearly diminished.

4. Highly precise sensors no longer need be selected since the circuit is self-compensating.

Figure 2:
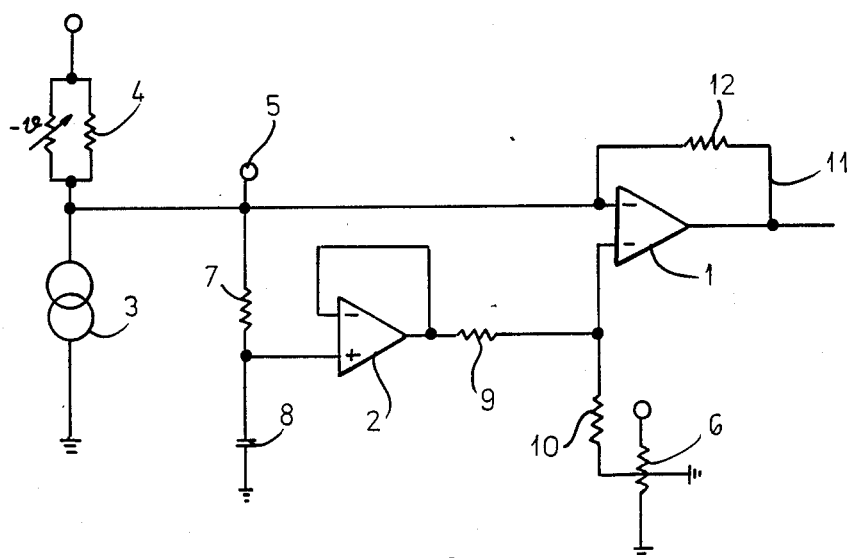
FIG. 2 the basic circuit diagram of a second embodiment.

The embodiment according to FIG. 2 is different from the one according to FIG. 1, in that it has an analog output, where the aforementioned compensation effect is present. In a negative feedback branch 11, a resistor 12 is provided. The result is that the signal follows an analog characteristic curve. As a consequence of the negative voltage, the generated analog signal functions as a correction voltage which pushes back and compensates for any slowing influences.

Figure 3:
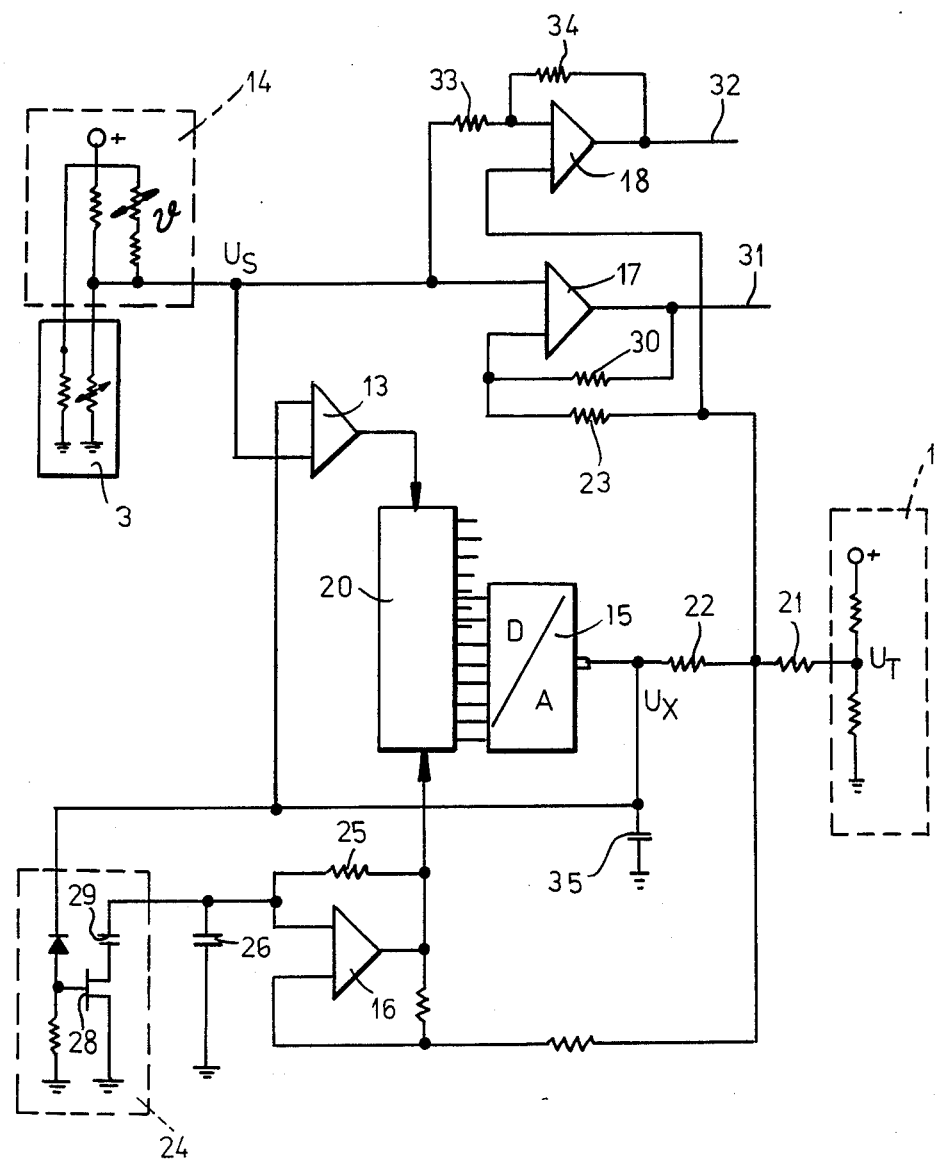
FIG. 3 the basic circuit diagram of a third embodiment.

The embodiment examples according to FIGS. 3-5 are based on the following concept which offers an extremely advantageous solution for the described problem.

Modification of the reference voltage by directing the signal over a low-pass filter, which is not entirely correct to describe as integration, results in peak values of pollut ant concentration, such as very frequently occur in practice in traffic conditions, leading easily to a very rapid adjustment of the reference voltage. An undesired effect may arise wherein the sensor, after a few pollutant impacts of correspondingly high value, becomes desensitized. Of course, there seems to be no actual reason for this, since, as known, the voltage increase at the exit of the low-pass filter is not only a function of the resistor and capacitor dimensions but also of the input voltage.

The circuit according to FIG. 3 avoids this disadvantage and superimposes a genuine integration signal on the reference voltage, which signal can have almost any chosen time factor. This is important considering that humidity- and temperature values change extremely slowly and that the subjective perception of the human sense of smell is related to time constants, which although individual, are generally pretty long.

In the embodiment example of FIG. 3, sensor 3 consists of a pollutant-dependent modifiable semiconductor resistor, which is heated. A voltage divider is formed from sensor 3 and a resistor combination 14. The latter can consist of a single resistor or of an arrangement as shown, whereby one of the resistors is a NTC-resistor, whose measurements are selected so that temperature-dependency of the sensor 3 is equal to the temperature variation range of the resistor combination 14. In a voltage divider the signal Us is obtained. The sensor signal Us reaches a comparator 17, whose reference voltage comes from a voltage divider 19, whose divider voltage Ut is mixed with a further signal over the resistor 21 and the resistor 22 and reaches the comparator 17 over a resistor 23. The sensor signal further reaches another comparator 13, to whose other input is brought an output signal of a digital-analog converter 15.

Output voltage of the digital-analog converter 15 is marked in the following as Ux. The digital-analog converter 15 is triggered by an up-and-down counter, which is triggered by a clock generator of any desired frequency. A clock frequency is so selected that when an 8-bit-converter is used, an eighth bit is reached after a time span which comes close to the previously described time constant, such as 3-10 minutes.

Counter 20 is an up-and-down counter. The up-and-down function results from the switch position of the comparator 13. When the operation starts, the counter shows invariably = a zero value. Also, the output signal Ux is = zero. However, the sensor signal Us has a positive value. Therefore, the comparator 13 is so connected that the output value assumes a value which will determine the counter 20 to start its count up. After a time span which depends on the clock frequency, the output voltage Ux of the digital-analog converter 15 reaches the value of the sensor voltage Us. At this point, the comparator 13 will switch and start to work on the countdown. So far, in a static situation, of the sensor voltage, the output voltage Ux of the digital-analog converter 15 oscillates around the value of the sensor voltage. When the sensor voltage varies, the output voltage Ux follows the sensor voltage linearly at a time interval which is determined by the frequency of the clock. So far, the output voltage Ux of the digital-analog converter 15 corresponds to a value which, as a continuous division with time-dependent division function, can be defined as a medium value integral of the sensor voltage. It is advantageous that the speed of change is constant and the value of the change (over time) is constant and does not depend on the sensor voltage.

The formula in FIG. 4 indicates the function of the output voltage Ux.

Superimposition of the reference voltage by the so-obtained correction voltage takes place through the addition of the divider voltage Ut and the voltage Ux at the resistor 22 and 21. The reference voltage can be calculated according to the formula shown in FIG. 5.

In a preferred embodiment, the resistors 21, 22 are so dimensioned that the reference voltage can be modified by a value of approximately ±30%. Other values can also be selected. As proven by experience, with such a selection of dimensions, for a start, the humidity drift of the sensor is overcome. This drift, which according to nature, happens extremely slowly, is pushed back by the circuit in a very reliable manner. When the pollutant concentration of the external air is very high, the reference voltage follows a tendency to change so that the switching function is shifted in the direction of "less sensitive". Likewise, the set-up becomes more sensitive towards pollutant peaks when the sensor is exposed to predominantly unpolluted external air. This way the shift of the switch point corresponds advantageously to the subjective perception of the human sense of smell.

It is an advantageous side effect that immediately after being switched on, the circuit is relatively insensitive because the output voltage Ux has first to build up. Since it is known that semiconductor sensors need a certain formation time, undesirable switching processes are counteracted.

In order to quickly bring up the output voltage Ux of the digital-analog converter 15 to a value corresponding to the typical sensor voltage, a set-up 24 can be inserted, which considerably accelerates this starting process. Clock frequency is basically determined by the time constant of the resistors 23, 25 and the capacitor 26. When the voltage Ux is still low, a Zener diode 27 is still blocking and as a result a FET-transistor 28 is still blocked. The capacitor 26 is selected so that the clock frequency is relatively high and the counter 20 having this way a rapid count-up. After the Zener voltage is reached, the transistor 28 becomes conductive and connects a capacitor 29 in parallel to the capacitor 26. This way the clock frequency is correspondingly slowed down. The advantage of this arrangement is that the circuit reaches very quickly its operational range, whereby additional expenditure on parts is minimal.

It should be pointed out that the aforedescribed basic circuit arrangement functions even when the latter-described steps have not been included.

The switch response can present a freely selectable hysteresis. Here the reference-voltage signal is not fed directly to the comparator 17 but via a series resistor 23, whereby through a further resistor 30 a positive feedback occurs.

Next to a switch output 31, an analog output 32 is implemented, whereby the sensor signal is transmitted to operation amplifier 18, whose amplification is determined by the resistors 33 and 34, whereby the noninverting input of the operation amplifier 18 is triggered with a reference-voltage signal Uref.

The digital-analog converter 15 can also be replaced by a R/2R-network.

The voltage at the output of the digital-analog converter 15 can be equalized by a capacitor 35.

The voltage divider 19 can consist at least partially of an adjustable resistor, in order to insure the free adjustability of the reference voltage.

The four operation amplifiers 13, 16, 17, 18 being utilized can be integrated in one casing.

Advantageously, the frequency generator 16 obtains its medium voltage from the voltage divider 19, which contributes to savings of parts.

With regard to the technical details of the circuit, it is possible to create other variants by using different parts, without modifying the basic concept of the invention.

Figure 6:
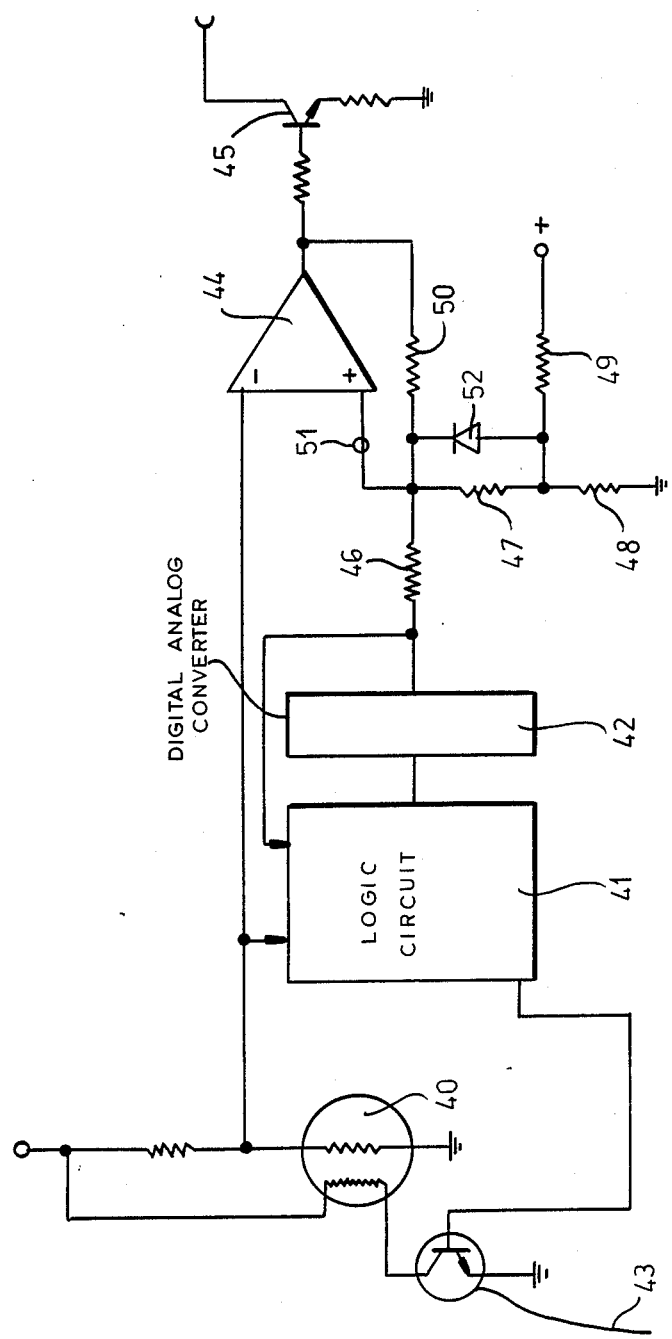
Figure 7:
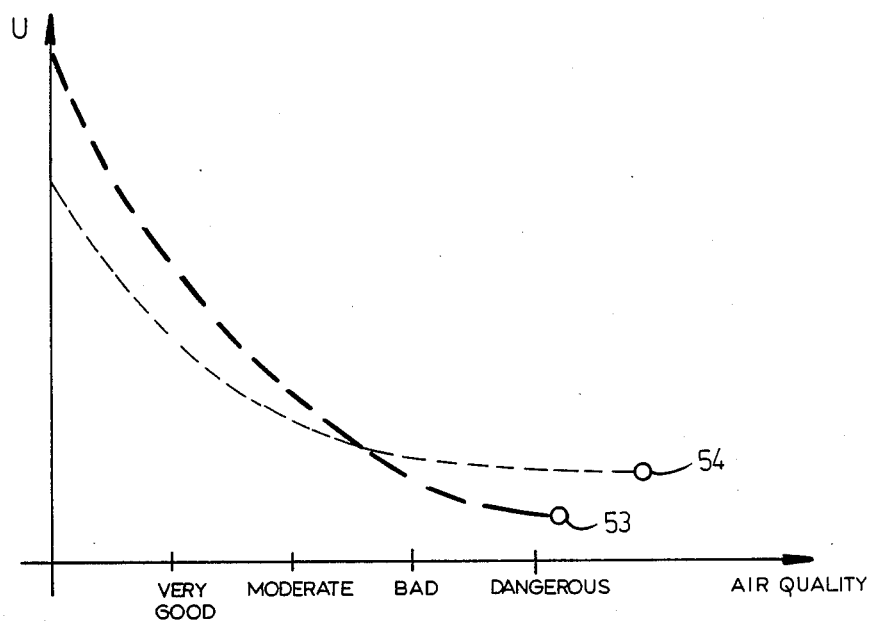
Figure 8:
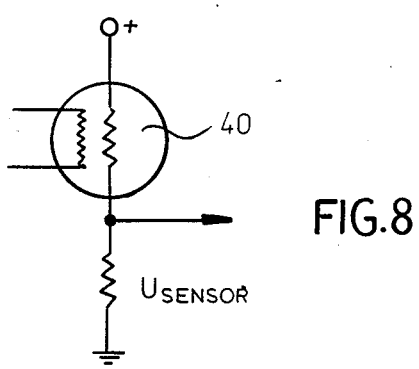

In the embodiment example according to FIGS. 6-8, there is illustrated a sensor 40, an integrated logic circuit 41, a digital-analog converter 42, a switch transistor 43 for heating the sensor, a comparator 44, a switch output 45 and resistors 46, 47, 48, 49, 50 of the voltage divider.

The resistor network produces a switch voltage, which in the range of good air to only moderately polluted air sets the switch voltage in such a way that comparator 44 does not switch.

In the range of bad or even dangerously polluted air, the switch voltage will be set in such a way that comparator 44 will switch in the case of static sensor voltage.

In the voltage divider 46-50, which lies at the reference voltage formed at the output of the digital-analog converter 42, a switch voltage 51 is built up, which lies at the noninverted input of the comparator 44. A diode 52 lies parallel to the resistor 47, and becomes conductive when a certain level is reached and strongly curves the characteristic curve of the switch voltage.

It could be desirable to curve the switch voltage even more so that as the static sensor voltage, and thereby the output voltage of the digital-analog converter 42, reaches a freely determinable value the diode 52 becomes conductive and generates a current flow from the digital-analog converter 42 through the resistor 46, the diode 52 and the resistor 49. This current flow clearly attenuates the slope of the switch voltage in this portion of the curve. Safety is thereby increased in the sense that in the presence of objectively dangerous pollutant concentrations the output will be constantly connected.

From FIG. 7 the diode effect can be understood. There is drawn a curve 53 for the sensor voltage and a curve 54 for the switch voltage 51.

It is also possible to arrange a sensor 40 as shown in FIG. 8. With this sensor arrangement the characteristic curve of the voltage is reversed with respect to the level of pollutants. The aforedescribed system remains valid when the polarity of the diode is inverted. The switch output is also inverted.

We claim:

1. A sensing system for controlling air circulation valves of motor vehicles, comprising:
   a pollutant detecting and electronic preconditioning sensor means which is a semiconductor, said means generating one or more signals related to a measured level of pollutants;
   a switch amplifier receiving said signals, said amplifier having a variable operating switchpoint dependent upon the received signals; and
   a means for integrating said one or more signals.

2. A sensing system according to claim 1 further comprising:
   a potentiometer;
   at least two resistors; and
   an integration resistor and a capacitor forming a part of said integrating means, and wherein voltages at output ends of said integrating means and said potentiometer causing a switch voltage at the switch amplifier are summed up across said at least two resistors, said resistors interrelating with one another and directing the switch amplifier to modify its switch point.

3. A sensing system according to claim 1 further comprising a negative feedback means through which said switch amplifier is wired, and wherein said one or more signals provided at an output end of said sensor means are analog signals.

4. A sensing system according to claim 1 wherein a threshold of said sensor means obeys a linear response and a time constant for said integrating means is a multiple of speed changes usually encountered in traffic-generated pollutant loads.

5. A sensing system according to claim 4 wherein said time constant ranges approximately between 2 and 5 minutes.

6. A sensing system according to claim 1 further comprising a voltage divider and a resistor network wherein a reference voltage is derived from said voltage divider and can be influenced by a correction voltage dependent upon a signal relayed over said resistor network by an amount which results from a resistance relationship between separate resistors of said network.

7. A sensing system according to claim 6 further comprising a binary counter means which generates a correction voltage to correct said reference voltage, a digital-analog converter means for reconverting the correction voltage into an analog signal, an oscillator means for feeding counter frequency to said binary counter means, a comparator means for comparing said analog signal with a sensor voltage and having an output voltage, said output voltage allowing said binary counter means to count either higher or lower depending upon whether said correction voltage is higher or lower, respectively, than said sensor voltage.

8. A sensing system according to claim 7 wherein said counter frequency is variable depending upon an output voltage of said digital analog converter in such manner that said frequency slows down with increasing output voltage of the digital analog converter and that after surpassing a freely selectable threshold value, an electronic switch connects an additional capacitor to said oscillator to slow down said oscillator.

9. A sensing system according to claim 8 further comprising a second voltage divider that includes at least one temperature-dependent resistor, said resistor being dimensioned so that the temperature-dependency thereof corresponds to a temperature-dependency of said sensor and any temperature drift of the sensor is compensated for by said resistor.

10. A sensing system according to claim 9 further comprising a first resistor, a second resistor and a further comparator means, said reference voltage travelling sequentially over said first and second resistors to obtain a positive feedback and then to said further comparator means, said travel resulting in a switching behavior which is a freely selectable hysteresis.

11. A sensing system according to claim 10, further comprising a switch output adjacent said further comparator means, an analog output adjacent said switch output, an operation amplifier, and a third and fourth resistor wherein said sensor signal travels to said operation amplifier whose amplification is determined between said third and fourth resistors and a non-inverting input of said operation amplifier is triggered with a further reference voltage.

12. A sensing system according to claim 11 wherein said amplifiers are integrated within a single housing.

13. A sensing system according to claim 7 wherein said converter presents a lower bit than said counter and said digital-analog converter is connected into said binary counter means in such manner that a lower bit of said counter means can be disregarded.

14. A sensing system according to claim 7 wherein said oscillator receives a medium voltage from said voltage divider thereby advantageously minimizing parts.

15. A sensing system according to claim 7 wherein a switching voltage at a non-inverting input of a comparator is created in a voltage divider lying at a reference voltage which is being generated at an output of a digital analog converter, whereby a diode connected in parallel with a resistor becomes conductive when a certain level is reached and strongly bends a curve characteristic of a switching voltage associated with said switch amplifier.

16. A sensing system according to claim 1 further comprising a voltage divider and a digital analog converter wherein a reference voltage is derived from said voltage divider and can be influenced by a correction voltage dependent on a signal relayed through said digital analog converter by an amount which results from a resistance relationship between said divider and converter.

17. A sensing system according to claim 16 wherein said digital analog converter is replaced by a R/2R-network.

18. A sensing system according to claim 16 wherein a voltage output of said digital analog converter is smoothed by a capacitor.

19. A sensing system according to claim 16 wherein said voltage divider can at least partially consist of an adjustable resistor for the purpose of free adjustability of the reference voltage.

* * * * *